United States Patent

Rangaswamy

(10) Patent No.: US 11,597,693 B2
(45) Date of Patent: Mar. 7, 2023

(54) PRODUCTION OF MALIC ACID USING TUBULAR AND STIRRED TANK REACTORS

(71) Applicant: THIRUMALAI CHEMICALS LIMITED, Mumbai (IN)

(72) Inventor: Parthasarathy Rangaswamy, Vellore (IN)

(73) Assignee: THIRUMALAI CHEMICALS LIMITED, Mumbai (IN)

( * ) Notice: Subject to any disclaimer, the term of this patent is extended or adjusted under 35 U.S.C. 154(b) by 0 days.

(21) Appl. No.: 17/655,146

(22) Filed: Mar. 16, 2022

(65) Prior Publication Data

US 2022/0234980 A1    Jul. 28, 2022

Related U.S. Application Data

(63) Continuation of application No. PCT/IN2020/050848, filed on Oct. 2, 2020.

(30) Foreign Application Priority Data

Oct. 4, 2019 (IN) .............................. 201921040419

(51) Int. Cl.
    *C07C 51/087* (2006.01)
    *C07C 51/367* (2006.01)
    *C07C 59/245* (2006.01)

(52) U.S. Cl.
    CPC .......... *C07C 51/087* (2013.01); *C07C 51/367* (2013.01); *C07C 59/245* (2013.01)

(58) Field of Classification Search
    CPC ..... C07C 51/25; C07C 51/087; C07C 51/367; C07C 59/145; C07C 57/145
    See application file for complete search history.

(56) References Cited

U.S. PATENT DOCUMENTS 3,379,756 A    4/1968 Ahlgren
3,379,757 A    4/1968 Winstrom et al.
(Continued)

FOREIGN PATENT DOCUMENTS

CN          1560016 A        1/2005
IN    201621024815 A    *    8/2016
(Continued)

OTHER PUBLICATIONS

Examination Report issued for Taiwanese Patent Application No. 109134410, dated Dec. 30, 2021 in 6 pages including English translation.
(Continued)

*Primary Examiner* — Yate' K Cutliff
(74) *Attorney, Agent, or Firm* — Knobbe, Martens, Olson & Bear, LLP

(57) ABSTRACT

A process for production of malic acid includes obtaining a feed that includes one or more of crude maleic anhydride, pure maleic anhydride, crude maleic acid, crude fumaric acid, pure maleic acid, pure fumaric acid, vent gas scrubber solutions from production of maleic anhydride, and vent gas scrubber solutions from production of phthalic anhydride. The feed is passed in a tubular reactor assembly to obtain a first product stream, which includes unreacted feed and malic acid. The feed is made to undergo hydration reaction in the tubular reactor assembly for a first predetermined time period, and further hydration of the first product stream is caused in a stirred tank reactor assembly for a second predetermined time period to obtain a final product stream, which includes the malic acid.

14 Claims, 3 Drawing Sheets

(56) References Cited

U.S. PATENT DOCUMENTS 5,210,295 A 5/1993 Ramsey et al.
7,820,856 B2 * 10/2010 Koizumi ............... C07C 51/252
562/533

FOREIGN PATENT DOCUMENTS

| IN | 201621024815 A | * | 8/2016 | ........... C07C 51/087 |
| IN | 201921028680 A | * | 1/2021 | ........... C07C 51/087 |
| IN | 201921028680 A | | 1/2021 | |
| JP | S57-10608 A | | 1/1982 | |
| WO | WO-2012081043 A1 | * | 6/2012 | ........... C07D 307/33 |

OTHER PUBLICATIONS

International Search Report and Written Opinion issued for PCT/IN2020/050848, dated Jan. 14, 2021 in 6 pages.
Indian Office Action issued for Indian Patent Application No. 201921040419, dated Apr. 5, 2022 in 6 pages.

* cited by examiner

PRODUCTION OF MALIC ACID USING TUBULAR AND STIRRED TANK REACTORS

CROSS-REFERENCE TO RELATED APPLICATIONS

This application is a continuation of International Application PCT/IN2020/050848, filed Oct. 2, 2020, which claims priority to Indian Patent Application No. 201921040419, filed Oct. 4, 2019. The disclosures of the above-described applications are hereby incorporated by reference in their entirety.

TECHNICAL FIELD

The present subject matter relates generally to the production of malic acid, and in particular to the production of malic acid from different raw materials starting from butane or benzene or ortho-xylene using tubular reactors and continuous stirred tank reactors (CSTR).

BACKGROUND

Malic acid is traditionally manufactured by the hydration of maleic acid, which is prepared by the dissolution of maleic anhydride in demineralized water or using a mixture of maleic acid and fumaric acid under conditions of high pressure and high temperature. The time taken to attain equilibrium, i.e., formation of an equilibrium mixture of malic acid, fumaric acid, and trace amounts of unreacted maleic acid, which is considered as the time to reach completion of the reaction for a given quantity of maleic acid or its isomer fumaric acid or a mixture thereof, varies from 4 to 8 hours.

Catalysts have been found to increase the productivity of malic acid in the aqueous hydration of maleic acid. In a typical hydration reaction, maleic acid is hydrated in the presence of various catalysts including sulfuric acid.

US3379756 describes a process for the synthesis of malic acid from maleic acid, fumaric acid, and mixtures thereof in an aqueous reaction mixture at elevated temperature and pressure wherein the process is performed in a reactor zone whose surfaces that are exposed to the reaction mixture consist of at least one material from the group of titanium, zirconium, tantalum, and alloys containing at least one of the said material.

U.S. Pat. No. 5,210,295 discloses a process for the hydration of an acid selected from maleic acid, fumaric acid and others, where the high temperature reaction is done in the presence of sodium ions in specified molar ratios.

U.S. Pat. No. 3,379,757 discloses a process for the manufacture of malic acid from aqueous solutions of maleic acid resulting from the vapor phase catalytic oxidation of an organic compound such as benzene comprising ageing the resulting maleic acid solution in the presence of air, filtering the aged solution and heating the filtrate in a closed system under super atmospheric pressure to convert the maleic acid to malic acid. This ageing process is carried in a rubber lined steel tower.

IN201621024815 discloses a process for preparation of malic acid in titanium tubular reactors. It further discloses that the tubular reactor of a particular design made with specific corrosion-resistant material like Titanium, with a high pressure circulating pump, prevents plugging and promotes high speed conversion.

However, the conventional methods of production of malic acid have several disadvantages. For example, very high temperatures and pressures are required for the reaction, it takes a long time for the reaction to reach equilibrium, the reaction products are corrosive and poisonous leading to corrosion of reactor vessels, and additional processes are required for removing contaminants from the products, leading to higher operating costs. Large reactor volumes are required at industrial scale Malic acid production by conventional methods.

SUMMARY

In an aspect of the present disclosure, there is provided a process for production of malic acid, the process comprising: (a) obtaining a feed comprising one or more of crude maleic anhydride, pure maleic anhydride, crude maleic acid, crude fumaric acid, pure maleic acid, pure fumaric acid, vent gas scrubber solutions from production of maleic anhydride, and vent gas scrubber solutions from production of phthalic anhydride; (b) passing the feed in a tubular reactor assembly to obtain a first product stream comprising unreacted feed and malic acid, wherein the feed is made to undergo hydration reaction in the tubular reactor assembly for a first predetermined time period; and (c) causing further hydration of the first product stream in a stirred tank reactor assembly for a second predetermined time period to obtain a final product stream comprising malic acid.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components where possible.

DETAILED DESCRIPTION

Figure 1:
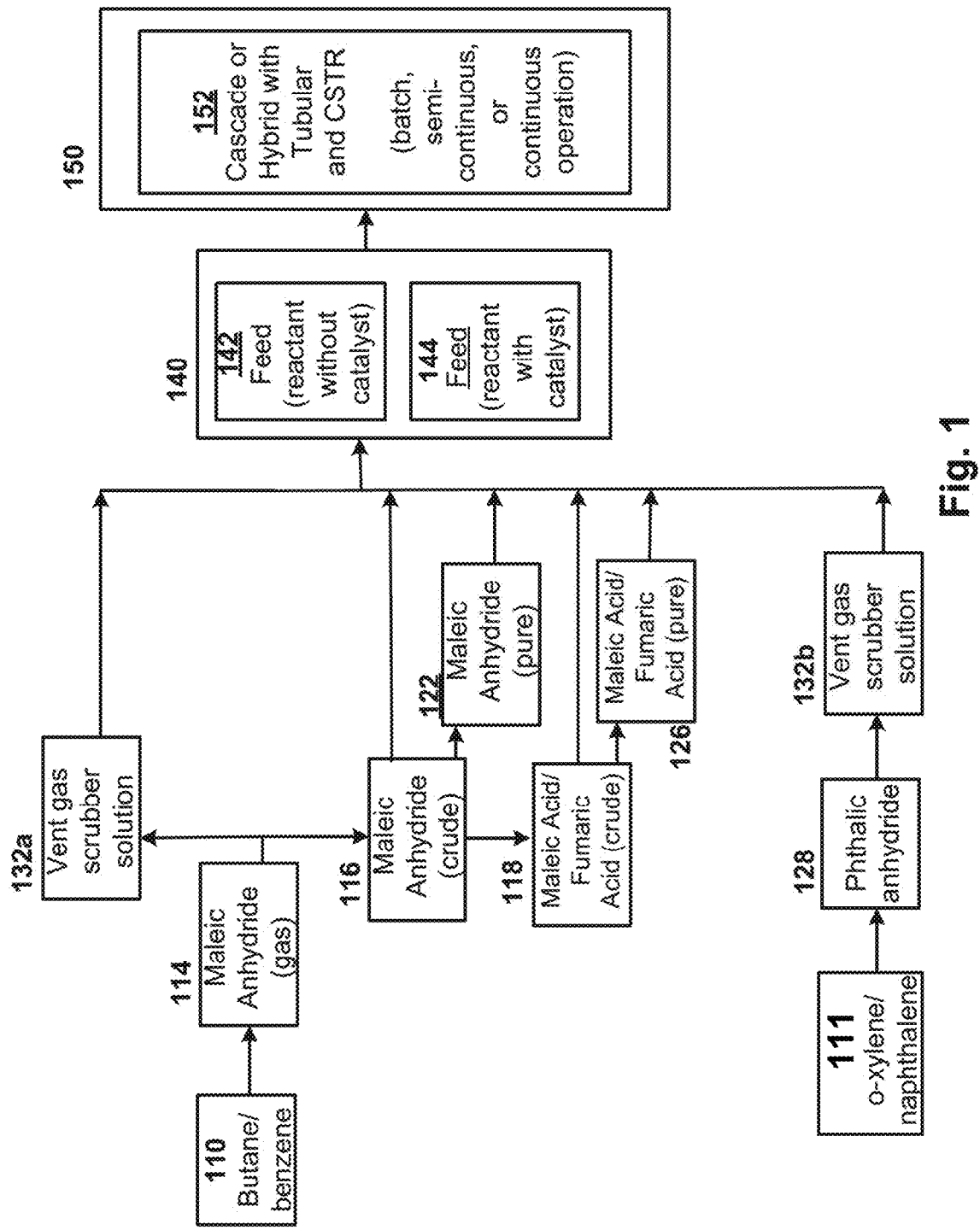
FIG. 1 illustrates a scheme of malic acid production, in accordance with an embodiment of the present subject matter.

The present subject matter relates to the production of malic acid from different raw materials and their mixtures in tubular reactors and continuous stirred tank reactors (CSTR).

Traditionally, malic acid is commercially produced using pure maleic anhydride obtained by the distillation of crude maleic anhydride, or from pure fumaric acid. The crude maleic anhydride or crude fumaric acid are obtained by vapor phase oxidation of organic compounds such as butane, benzene, furan, furfural, and the like. The gaseous mixture of mainly maleic anhydride released from the outlet of the reactor is cooled in a condenser to obtain a material, which is known as crude maleic anhydride. This crude maleic anhydride is subjected to distillation to produce pure maleic anhydride. The uncondensed gases exiting the condenser are scrubbed in water to produce crude maleic acid, called as scrubber solution. This maleic acid scrubber solution is further subjected to azeotropic distillation with o-xylene to produce crude maleic anhydride followed by vacuum distillation to produce pure maleic anhydride. The pure maleic anhydride is then used for the production of malic acid.

However, purification of maleic anhydride using conventional reactors is a time consuming, and energy-intensive method. Moreover, using the pure form of maleic anhydride leads to a great increase in the cost of malic acid production. Additionally, conventionally used reactors configuration do not properly incorporate the key features of all the smaller scales, thereby making the method of purification of maleic anhydride expensive.

The production of malic acid of the present subject matter overcomes the problems and disadvantages associated with conventional methods of production of malic acid. The present subject matter relates to production of malic acid and co-production of fumaric acid from butane or benzene or from any other intermediate products formed during the production of maleic anhydride or phthalic anhydride. Crude products formed during production of maleic anhydride, phthalic anhydride, maleic acid, fumaric acid, and the like, and uncondensed vent gases recovered by dissolving in water, generally called scrubber solution, may be used, in addition to using the pure forms of these products as the raw materials. In one example, for purification of crude products, any one or more of the following processes known to those skilled in the art can be followed: adsorption, absorption, spray drying techniques, and falling film evaporation. The production can be done in continuous, semi-continuous, batch modes, or any combination thereof. The reactors may include an arrangement of tubular and continuous stirred tank reactors, which may be used in any combination to form a hybrid or cascade set of reactors. Further, the combination of reactors may be used for production in one of a continuous, semi-continuous, or batch mode. The combination of reactors allows for a reduction in size of the total reactor system volume (cumulative) for a given quantity of Malic acid produced, compared to when using only a single stirred tank reactor or a single tubular reactor, for the same reaction conditions and same level of conversion.

The method does not require pure raw materials, as required in conventional methods, thus reducing costs significantly. The method also reduces the amount of effluent to be treated during production of pure maleic anhydride or pure maleic or fumaric acids. The method also reduces the time for the reaction to about 1-3 hours depending on the reactor assembly. The reduction in time reduces the energy consumed during operations and thus reduces operating costs.

In one embodiment, the reactor assembly used is a combination of tubular reactor and stirred tank reactor operated in continuous, semi-continuous, or batch mode. The process of the present disclosure can be carried out in a tubular reactor of suitable design to prevent plugging and promote high rate of conversion by maintaining a turbulent flow with Reynold's number from about 2900 to about 10000. In some embodiments, the flow in the reactor can have Reynold's number from about 3000 to about 9000, from about 4000 to about 8000, from about 5000 to about 8000, from about 5000 to about 7000, from about 5500 to about 7000, or from about 6500 to about 7000. In some embodiments, the Reynolds number may be, for example, at least 2500, 3000, 3500, 4000, 4500, 5000, 5500, 6000, 6500, 7000, 7500, 8000, 8500, 9000, 9500, 10000, or within a range defined by any two of the aforementioned Reynolds numbers. In another embodiment passing the feed through the tubular reactor assembly comprises passing the feed in a tubular reactor at a Reynold's number from about 5000 to about 7000. The reactor may be made up of titanium, and thus be corrosion resistant.

The present disclosure provides a method for production of malic acid, wherein the feed is reacted in a reactor assembly comprising a combination of one or more tubular reactors (referred to as tubular reactor assembly) and one or more continuous stirred tank reactors (CSTRs) (referred to as stirred tank reactor assembly). The feed may be selected from crude maleic anhydride, pure maleic anhydride, crude maleic acid, crude fumaric acid, pure maleic acid, pure fumaric acid, vent gas scrubber solutions from the production of maleic anhydride from an organic compound such as butane, benzene, vent gas scrubber solutions from production of phthalic anhydride from an organic compound such as o-xylene or naphthalene, and any combinations thereof. The reactor assembly may be one of a hybrid reactor system or a cascade reactor system. The feed may be reacted in the reactor assembly at 145-200° C. and 11-15 bar for about 1-3 hours to obtain a mixture of malic acid and fumaric acid. In the hybrid system, feed may be continuously circulated through the reactor assembly, whereas in the cascade system, feed may be fed to a first tubular reactor and reacted for a preset amount of time, then to a next tubular reactor or CSTR reactor, and so on until reaction completion. Any number of tubular or CSTR reactors can be used so that the feed is first reacted in the set of tubular reactors and then in the set of CSTR reactors. The tubular reactor(s) may comprise a set of tubes with arrangements such as loops of tubes, circular tubes, or spherical arrangement of tubes, and twisters and swirlers. The reaction of feed in the reactor may be performed in the presence of a catalyst or without a catalyst. In case the catalyst is used, the catalyst may comprise aluminum metal, its borate or carbonate salts in the micronized form. The reaction in the hybrid system may be performed in one of a batch mode, semi-continuous mode, or continuous mode. In the batch mode, after reaction completion in the reactor assembly, the solution is drained and taken for further processes. In the semi-continuous mode, a part of the solution is drained after some time and equal quantity of feed solution containing the catalyst is fed into the tube, recirculated and again after a fixed period of time another fixed quantity is drained, and the process is repeated, whereas in the continuous mode, a very small quantity of the solution is drained into a flash tank continuously and simultaneously the same quantity of feed solution containing the catalyst is fed into the tubes.

Aspects of the present subject matter are further described in conjunction with the appended figures. It should be noted that the description and figures merely illustrate the principles of the present subject matter. It will thus be appreciated that various arrangements that embody the principles of the present subject matter, although not explicitly described or shown herein, can be devised from the description and are included within its scope. Moreover, all statements herein reciting principles, aspects, and implementations of the present subject matter, as well as specific examples thereof, are intended to encompass equivalents thereof.

In an embodiment of the present disclosure, there is provided a process for production of malic acid, the process comprising: (a) obtaining a feed comprising one or more of crude maleic anhydride, pure maleic anhydride, crude maleic acid, crude fumaric acid, pure maleic acid, pure fumaric acid, vent gas scrubber solutions from production of maleic anhydride, and vent gas scrubber solutions from production of phthalic anhydride; (b) passing the feed in a tubular reactor assembly to obtain a first product stream comprising unreacted feed and malic acid, wherein the feed is made to undergo hydration reaction in the tubular reactor assembly for a first predetermined time period; and (c) causing further hydration of the first product stream in a stirred tank reactor assembly for a second predetermined time period to obtain a final product stream comprising malic acid. In another embodiment of the present disclosure, the final product stream may comprise malic acid. In one example, the final product stream comprises malic acid and co-product fumaric acid.

In an embodiment of the present disclosure, there is provided a process for production of malic acid as described herein, wherein the process comprises recirculating a second product stream obtained from the stirred tank reactor assembly through steps (b) and (c) for a predefined number of cycles prior to obtaining the final product stream.

In an embodiment of the present disclosure, there is provided a process for production of malic acid as described herein, wherein the process comprises removing a portion of a second product stream obtained from the stirred tank reactor assembly as the final product stream and recirculating a remaining portion of the second product stream obtained from the stirred tank reactor assembly through steps (b) and (c) along with fresh feed. The term "recirculation" as used herein implies circulation of an outlet stream back to any of the previous stages or for mixing with a fresh unreacted inlet stream.

In an embodiment of the present disclosure, there is provided a process for production of malic acid as described herein, wherein the portion of the second product stream is drained continuously.

In an embodiment of the present disclosure, there is provided a process for production of malic acid as described herein, wherein the portion of the second product stream is drained at predefined time intervals.

In an embodiment of the present disclosure, there is provided a process for the production of malic acid as described herein, wherein the portion of the second product stream is drained completely and not recirculated.

In an embodiment of the present disclosure, there is provided a process for production of malic acid as described herein, wherein the tubular reactor assembly comprises a single tubular reactor.

In an embodiment of the present disclosure, there is provided a process for production of malic acid as described herein, wherein the tubular reactor assembly comprises a plurality of tubular reactors connected in series.

In an embodiment of the present disclosure, there is provided a process for production of malic acid as described herein, wherein the tubular reactor assembly comprises a plurality of tubular reactors connected in parallel.

In an embodiment of the present disclosure, there is provided a process for production of malic acid as described herein, wherein the tubular reactor assembly comprises a plurality of tubular reactors connected in a series or parallel combination.

In an embodiment of the present disclosure, there is provided a process for production of malic acid as described herein, wherein the stirred tank reactor assembly comprises a single stirred tank reactor.

In an embodiment of the present disclosure, there is provided a process for production of malic acid as described herein, wherein the stirred tank reactor assembly comprises a plurality of stirred tank reactors connected in series.

In an embodiment of the present disclosure, there is provided a process for production of malic acid as described herein, wherein the stirred tank reactor assembly comprises a plurality of stirred tank reactors connected in parallel.

In an embodiment of the present disclosure, there is provided a process for production of malic acid as described herein, wherein the stirred tank reactor assembly comprises a plurality of stirred tank reactors connected in a combination of series and parallel arrangement.

In an embodiment of the present disclosure, there is provided a process for production of malic acid as described herein, wherein the process comprises adding a catalyst to the feed prior to passing the feed through the tubular reactor assembly.

In an embodiment of the present disclosure, there is provided a process for production of malic acid as described herein, wherein the catalyst is selected from a group consisting of aluminum metal, borate salt of aluminum, and carbonate salt of aluminum.

In an embodiment of the present disclosure, there is provided a process for production of malic acid as described herein, wherein the feed to catalyst ratio is in a range of about 1:0.00005 to about 1:0.0005.

In an embodiment of the present disclosure, there is provided a process for production of malic acid as described herein, wherein passing the feed through the tubular reactor assembly comprises passing the feed in a tubular reactor at a Reynold's number from about 2900 to about 10000, and preferably from about 5000 to about 7000.

In an embodiment of the present disclosure, there is provided a process for production of malic acid as described herein, wherein the feed is reacted at a temperature in a range of about 135-195° C. and a pressure of about 11-15 bar in each tubular reactor of the tubular reactor assembly and each stirred tank reactor of the stirred tank reactor assembly. The overall reaction time is 1 to 3 hours.

In an embodiment of the present disclosure, there is provided a process for production of malic acid as described herein, wherein the process comprises purifying the final product stream to obtain pure malic acid.

In an embodiment of the present disclosure, there is provided a process for production of malic acid as described herein, wherein the process comprises purifying the feed prior to passing the feed through the tubular reactor assembly. The purification may be carried out by conventional purification processes.

In an embodiment of the present disclosure, there is provided a process for production of malic acid as described herein, wherein the process comprises adding steam to the tubular reactor assembly and the stirred tank reactor assembly for causing the hydration reaction.

FIG. 1 illustrates a scheme of malic acid production, in accordance with an embodiment of the present subject matter. In one embodiment, the starting raw material 110 is butane or benzene. In another embodiment, the starting raw material 111 is one of o-xylene or naphthalene. In one example, butane or benzene is reacted in the vapor phase to produce crude maleic anhydride gas 114, in the presence of a catalyst. The crude maleic anhydride gas 114 is condensed to produce crude maleic anhydride 116. The reaction may also produce crude maleic acid 118, when the reaction product vapors are dissolved in water. The crude maleic acid 118 may be a mixture of maleic acid and fumaric acid. The crude maleic anhydride 116 may further be hydrolyzed to form crude maleic acid 118. The crude maleic acid 118 or the crude maleic anhydride 116 may be purified to obtain pure maleic acid 126 and pure maleic anhydride 122, respectively. The pure maleic acid 126 may be a mixture of pure maleic acid and pure fumaric acid. Along with the crude maleic anhydride 116, uncondensed vent gases are produced. The uncondensed vent gases are passed through a scrubber to form a solution, herein referred to as vent gas scrubber solution 132*a*. The vent gas scrubber solution 132*a* comprises maleic anhydride, maleic acid, any unreacted raw material 110, and any other impurities.

In another embodiment, the raw material 111 is o-xylene or naphthalene. The raw material is reacted to produce phthalic anhydride 128. The product gases that are not condensed are passed through water to form another vent gas scrubber solution 132*b*, generally comprising any unreacted raw material 111, phthalic anhydride 128, and any other impurities.

The feed 140 for production of malic acid may be selected from the group consisting of crude maleic anhydride, pure maleic anhydride, crude maleic acid, crude fumaric acid, pure maleic acid, pure fumaric acid, vent gas scrubber solutions from the production of maleic anhydride from an organic compound such as butane, benzene, vent gas scrubber solutions from production of phthalic anhydride from an organic compound such as o-xylene or naphthalene, and any combinations thereof.

The crude fumaric acid may be obtained from any of maleic anhydride, maleic acid, as a by-product of phthalic anhydride production, or by bio-technology routes known in the art.

The feed undergoes reaction to produce a mixture of malic acid and fumaric acid at a temperature range of 145-200° C. and a suitable pressure. The reaction may be carried out either in the presence of a catalyst or without a catalyst. In one embodiment, feed 142 undergoes reaction in the absence of any catalyst. In another embodiment, the feed 144 is a feed stream with catalyst and undergoes reaction in the presence of the catalyst. The catalyst is selected from aluminum metal or its borate or carbonate salts in its micronized form such that the use of the catalyst causes no corrosion in the inner surface of the reactor vessel, thus ensuring the catalytic process is corrosion free. The use of the alternative aluminum borate solution results in the formation of boric acid. Since boric acid is a weak acid, it does not corrode the reactors.

The concentration of the catalyst used in the reaction affects the process time, rate of reaction to attain equilibrium, and requirement of additional purification steps for removal of the catalyst used. In the catalytic process, the concentration of aluminum metal or aluminum borate or aluminum carbonate in its micronized form is in the range of 50-500 mg/l with respect to the crude maleic anhydride solution in the feed. The micronized aluminum metal or its borate salt or carbonate salt in its powder or granular form has a particle size of 10 microns to 800 microns. The aluminum metal or its borate or carbonate salt solubilized in the feed 140 significantly speeds up the reaction to equilibrium. In one example, the ratio of crude maleic acid to the catalyst is 1:0.0001 in the resulting solution.

The feed 140 may be reacted in a reactor assembly 150. The reactor assembly 150 may comprise a combination of tubular reactors (i.e., tubular reactor assembly) and continuous stirred tank reactors (i.e., stirred tank reactor assembly) in cascade or hybrid configuration 152. The reactor assembly 150 may be configured to operate in any one of a continuous mode, semi-continuous mode, batch mode, or any combination thereof. The reactions may be performed either in the presence or absence of catalyst. Hybrid reactor configuration has operational flexibility due to piping connections back to the inlet and intermediate streams, whereas cascade reactor configuration is operated in a batch mode.

The tubular reactors that are part of the cascade or hybrid reactor systems 152 may be made of suitable material and operated in varying modes such as continuous, semi-continuous, or batch mode. The tubular reactors used for the production of malic acid from the feed solution are designed suitably to prevent plugging and promote high speed conversion. The reactors may be made of a suitable material of construction such as titanium, tantalum, Hastelloy, Aluminum-Bronze or zirconium. A high-pressure circulating pump in the hybrid assembly allows for feeding and recirculating the solution, which may comprise feed and partially reacted feed. The feed end of the tubular reactor is connected to the pump, while the other end is connected back to the suction of the pump for continuous circulation at pressure, with a bypass valve. Alternatively, there is a bypass in the piping after the tubular reactor for removal of all or some material into a flash tank or a drain tank. The flash tank may also be connected back to the circulating pump suction.

The tubular reactors may have an arrangement of tubes such as a loop of tubes, circular tubes, or spherical arrangement of tubes, which can enhance the rate of reaction and consequently reduce the processing hours to attain the production of malic acid in stoichiometric yield. The set of tubes in the tubular reactor are so arranged and interconnected and are provided with twisters and swirlers so as to provide a stream velocity of about 1.25 to 2.5 m/s, which leads to stoichiometric conversion of the feed material to the final equilibrium in reduced process time.

In an embodiment, the feed solution is pumped in to the tubular reactor assembly, circulated through the circulation pump, and discharged into the tubular reactor assembly at high velocity. The solution is continuously circulated through the tubes and is heated to a temperature of 145-200° C. at a pressure of 11-15 bar for about 1-2 hours. In another embodiment, when the process is conducted in the presence of catalyst, aluminum metal or its borate or carbonate salt solution is added to the feed solution, prior to pumping in to the tubular reactor, so that the ratio of feed solution to the catalyst is 1:0.0001 in the resulting solution.

Further, the partially reacted feed may be passed through one or more continuous stirred tank reactors (CSTR) that may be connected in series with the tubular reactors. The partially reacted feed may be continuously stirred in the CSTR tank by a stirrer or agitator for the desired period of time to ensure near complete stoichiometric conversion of the reactants into products. From the CSTR, the products are drained via a product outlet, any condensate is drained via condensate outlet, and gases are removed via vapor outlet.

The reactions in the tubular reactors and the CSTRs may be carried out in the presence of catalyst, such as aluminum metal or borate or carbonate salts of aluminum, or in the absence of catalysts. The production process in hybrid configuration can be carried out in any one of a batch process, semi-continuous process, or a continuous process. In the batch process, after the above operations, the solution is drained into a flash tank and taken for further processing, such as purification, filtration, and separation of the products. In the semi-continuous process, after the above operations, a part of the solution is drained and equal quantity of feed solution containing the catalyst is fed into the tube, recirculated and again after a fixed period of time another fixed quantity is drained, and the process is repeated. The drained solution is taken for further processing as mentioned with reference to the batch process. In the continuous process, after the above operations, a very small quantity of the solution is drained into a flash tank continuously and simultaneously the same quantity of feed solution containing the catalyst is fed into the tubes. The drained solution is taken for further processing as mentioned with reference to the batch process.

The reaction products obtained include a mixture of fumaric acid and malic acid. The two acids are separated from the mixture by conventional means. The volatile impurities and the color-causing compounds originating from crude maleic anhydride and the scrubber solution are drained by conventional purification processes. The mother liquor containing malic acid is concentrated to recover malic acid, which is further purified. The purification of the resulting malic acid can be carried out by a variety of means, including but not limited to, the use of ion exchangers, activated carbon in powder form, or passing malic acid through a series of carbon columns.

The boric acid formed when aluminum borate is used as a catalyst is removed from the mixture by processes known in the art.

While tubular reactors can be operated at high Reynolds flow conditions to increase the reaction speed, the length of the tubes to be used to ensure completion of reaction may be very high and not practically feasible and uneconomical from the viewpoint of fabrication, transportability as necessary. On the other hand, the time taken for attaining the equilibrium in CSTR is much slower, particularly at industrial scale. Furthermore, when a CSTR alone is used, the size of the CSTR required is very high to achieve a similar amount of conversion at similar reaction conditions, compared to when the CSTR is used in combination with tubular reactors. Hence, by using a combination of tubular reactors and CSTRs, in cascade or hybrid configurations, the present subject matter allows for advantageously obtaining the benefits of both tubular and CSTR reactors for efficient production of malic acid.

The experimental data show that the reactor assembly configurations and modes of operation described herein improve the productivity of malic and fumaric acids in terms of kg/h produced per unit volume (kl) of the reactor assembly compared to conventional reactor configurations and corresponding modes of operation known in the art.

Figure 2:
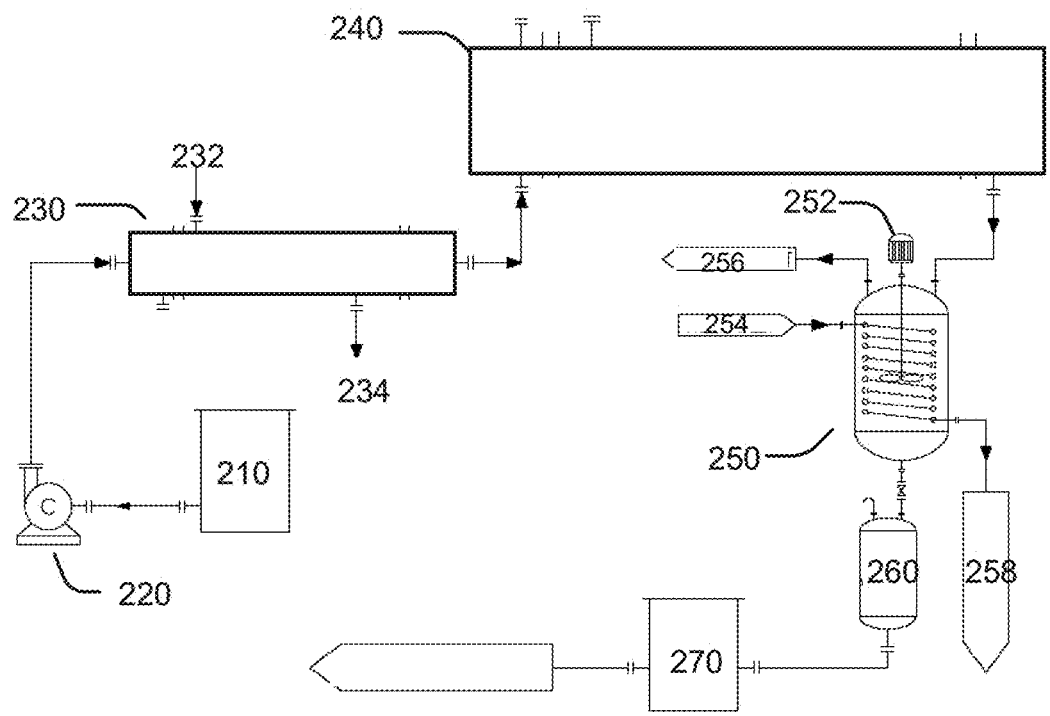
FIG. 2 illustrates a cascade reactor system for production of malic acid, in accordance with an embodiment of the present subject matter.

FIG. 2 illustrates a cascade reactor system for production of malic acid, in accordance with an embodiment of the present subject matter. Feed from feed tank 210 is fed to tubular reactors via a circulation pump 220. The figure shows two tubular reactors 230 and 240. However, it will be understood that any number of tubular reactors may be used. The feed is reacted in the first tubular reactor 230 for a preset amount of time at a certain temperature. In one example, the feed is reacted at 145-200° C. for 60-120 minutes. Steam is fed into the reactor 230 via a steam inlet 232 and any condensates are drained via condensate outlet 234. After a preset time, the solution or slurry is fed into the second reactor 240, where the reaction continues. After another preset time, the mixture is sent to a third reactor 250 for further reaction.

In one embodiment, the reactors 230 and 240 are tubular reactors and the reactor 250 is a stirred tank reactor. The reactant-product mixture in reactor 250 is stirred via a stirrer or agitator 252 and the reaction proceeds at preset conditions of temperature and pressure and for a preset time. In an example, the reaction may proceed at 145-200° C. at 10-15 bar. The reactor 250 comprises an inlet 254 for steam and outlet 256 for removing vapors and outlet 258 for removing any condensates. The product slurry is drained into a flash tank 260 after reaction completion, as the reactor 250 is depressurized and the products 270 are sent for further processing such as purification. Although the figure illustrates two tubular reactors and one stirred tank reactor, any number of such reactors may be used in any combination. The process may be operated in batch mode.

In one embodiment, the first and the second predetermined time periods/preset time may be set such that total reaction time is 1-3 hrs. Accordingly, the time for reaction in each reactor (tubular or stirred tank) may vary between about 15 mins to about an hour.

Figure 3:
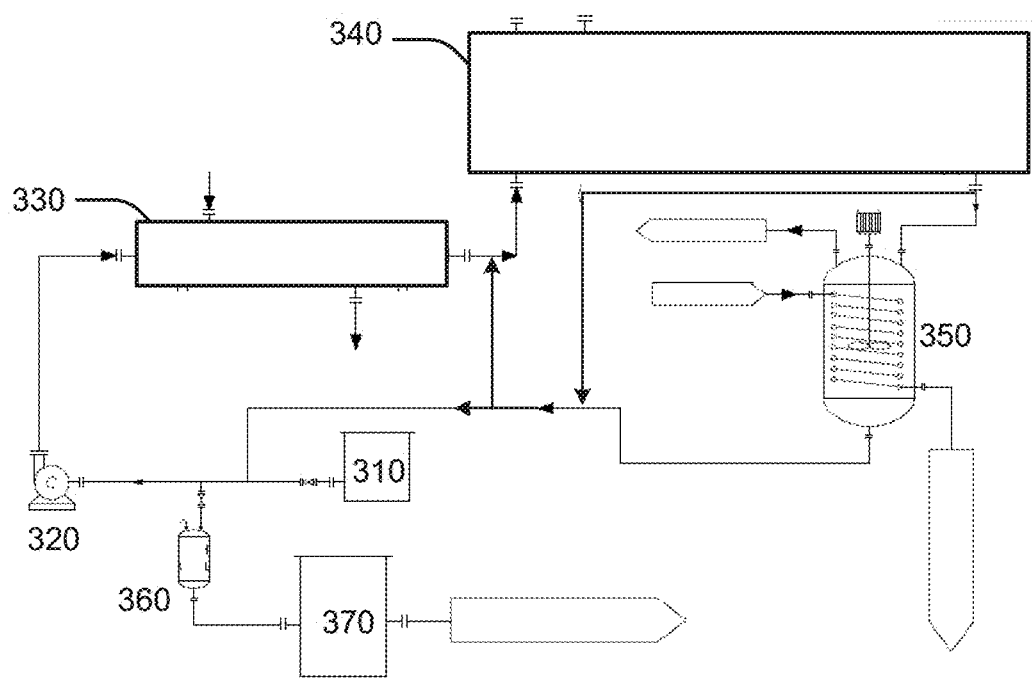
FIG. 3 illustrates a hybrid reactor system for the production of malic acid, in accordance with an embodiment of the present subject matter.

FIG. 3 illustrates a hybrid reactor system for the production of malic acid, in accordance with an embodiment of the present subject matter. Feed from feed tank 310 is passed through a series of reactors and the mixture is continuously circulated through the reactor system using circulation pump 320 for a preset time. The reaction occurs at predefined temperatures and pressures. In an example, the reaction may proceed at 145-200° C. at 10-15 bar. As shown in FIG. 3, the reactor system comprises two tubular reactors 330 and 340 and one stirred tank reactor 350 connected in series. However, any number of the two types of reactors, tubular and stirred tank reactors, connected in any combination may be used. The reactors may be operated in any one of a continuous mode, semi-continuous mode, or a batch mode. After the reaction is complete, the product slurry is drained into a flash tank 360 and the products 370 are sent for further processing.

In the cascade reactor configuration, as discussed with reference to FIG. 2, the feed solutions are fed through each reactor stage and it is allowed to react for a certain time in a reactor stage and then moved to the next reactor stage. The product is drained after reaction in the final reactor stage. The reactors operate in the batch mode of operation, where the feed is sent on to the next stage after partial conversion, and the final product is drained after reaction in the last reactor stage.

In the hybrid reactor configuration, the feed solution is circulated through the series of reactors with provision for recirculation. In the batch process in the hybrid configuration, the final product is drained after completion of the reaction. In the semi-continuous process in the hybrid configuration, a certain quantity of the product is drained into the flash tank 360 after reaction has proceeded for some amount of time. The same quantity of feed is fed in the reactors. In the continuous process, after reaction completion, an amount of product is drained out at a certain rate continuously and the same quantity of feed solution is added continuously. For both the cascade and hybrid reactor configurations, the reaction may be performed either in the presence or absence of a catalyst. When a catalyst is used, the time to attain reaction equilibrium is reduced further than when 20 no catalyst is used.

In one embodiment, for both the hybrid and cascade reactor configurations, the first and the second predetermined time periods/preset time may be set such that total reaction time is 1-3 hrs. Accordingly, the time for reaction in each reactor (tubular or stirred tank) may vary between about 15 mins to about an hour.

Figure 4A:
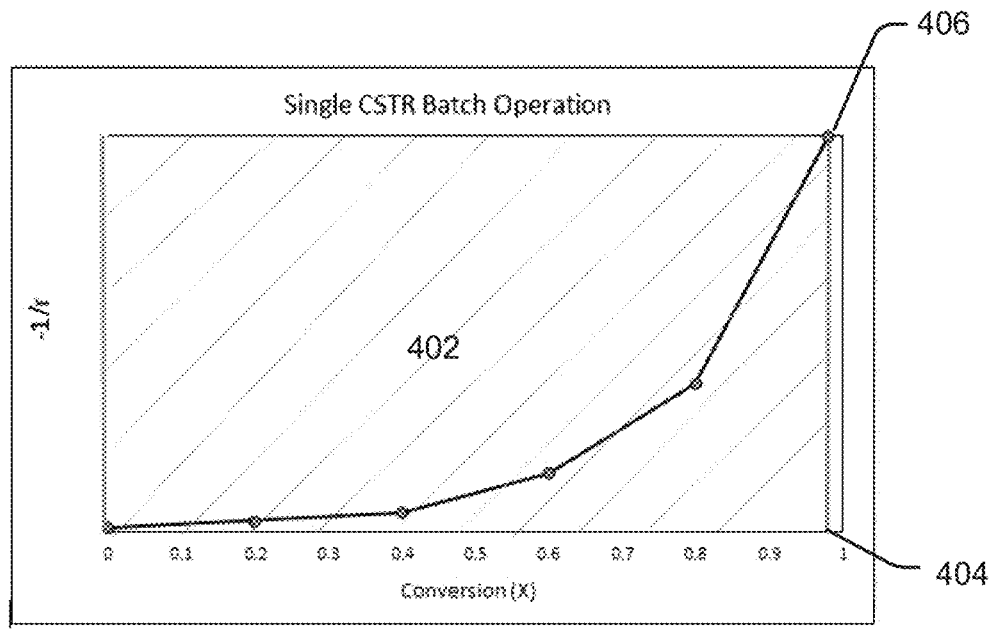
FIG. 4(a) illustrates an indicative Levenspiel plot for single CSTR reactor and FIG. 4(b) illustrates an indicative Levenspiel plot for CSTR reactor coupled with multiple tubular reactors, in accordance with an embodiment of the present subject matter.
Figure 4B:
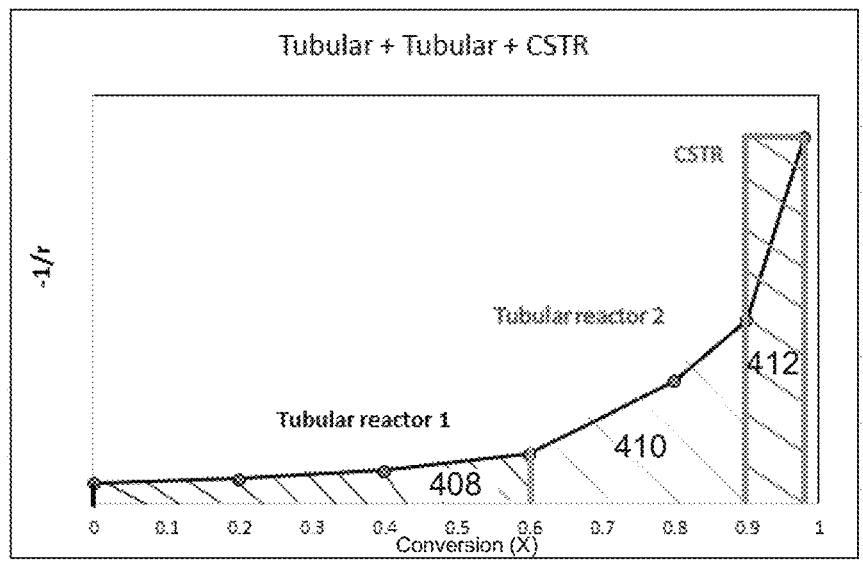

FIG. 4(a) illustrates an indicative Levenspiel plot for a single CSTR reactor and FIG. 4(b) illustrates an indicative Levenspiel plot for a CSTR reactor coupled with multiple tubular reactors, in accordance with an embodiment of the present subject matter. In FIGS. 4(a) and 4(b) the x-axis corresponds to the conversion (X) and the y-axis corresponds to $-1/r$, where r is the rate of reaction. As the conversion (X) increases, the concentration of the feedstock decreases. As would be understood by a person skilled in the art, the volume of a CSTR necessary to achieve a certain conversion at given reaction conditions, is equal to the area of the rectangle with height being proportional to (−1/r) and width equal to X. The volume of a tubular reactor required to achieve a certain conversion at given reaction conditions is equal to the area under the curve of (−1/r) plotted against X.

As shown in FIG. 4(a), for a single CSTR reactor operating in batch mode, the reactor volume required to achieve stoichiometric conversion is derived from the shaded area of the plot marked as 402, which corresponds to an area of the rectangle with width equal to X, corresponding to point 404, and height corresponding to (−1/r), or the y co-ordinate corresponding to the amount of conversion X, at point 406. The same method can be followed to derive the reactor volume of CSTR required for any specific conversion value along the x-axis.

Referring to FIG. 4(b), when tubular reactors are coupled with a CSTR reactor, when using the tubular reactors, at same reaction conditions, and for the same amount of conversion, a lesser reactor volume is required compared to that of a single CSTR. For example, when two tubular reactors are used with a CSTR reactor, a conversion of 0.6 can be achieved by tubular reactor one, as indicated by the shaded region marked as 408, and the volume of reactor required may be determined from the plot, which corresponds to an area under the curve. The shaded region denoted by 410, or the area under the curve, indicates the conversion achieved by a second tubular reactor and the corresponding reactor volume. The shaded region denoted as 412, which forms a rectangle, corresponds to the CSTR reactor, and the CSTR reactor volume required is area of the rectangle. Thus, the total combined reactor system volume required for the same amount of complete conversion as per stoichiometry, for the same reaction conditions, as shown in FIG. 4(b) is significantly lesser than that of a single CSTR as shown in FIG. 4(a), leading to reduced capital and operating costs.

Examples

The disclosure will now be illustrated with working examples, which are intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

Type 1: With Recirculation (Hybrid Configuration)
Modes of Operation: Batch, Semi-Continuous and Continuous.
  Experimental Details:
  Maleic Acid solution: 77 liters (or) Fumaric Acid Solution: 77 liters
  Concentration of Maleic Acid solution/Fumaric acid in water: 45% w/v
  Catalyst: 100 mg/liter (ppm) of Aluminum Borate
  Reaction Temperature: 185° C.
  Reactor Pressure: 12 bar.
  Feedstock:
  Three different feedstock compositions are shown in Table 1.

TABLE 1

Feedstock compositions

Feedstock 1 - Pure Maleic acid + Water/Pure Fumaric acid + Water/Mixture of these in any proportion or combination - feedstock is derived from n-Butane or Benzene.
Feedstock 2 - Crude Maleic acid + Water/Crude Fumaric acid + Water/Mixture of these in any proportion or combination - feedstock is derived from n-Butane or Benzene.
Feedstock 3 - Maleic Acid Scrubber Solution + Crude Fumaric acid + Water/Mixture of these in any proportion or combination - feedstock can be derived from O-Xylene or Naphthalene or n-Butane.

The feedstock in these experiments can be defined as any one of the following:
1. 29.27 kg of pure maleic anhydride dissolved in 60 liters of demineralized water so that the quantity of maleic acid is 34.65 kg.
2. 34.65 kg of pure fumaric acid.
3. A mixture of items 1 and 2 in any proportion or combination in that the quantity of such mixture is equivalent to 34.65 kg of maleic acid.

Experimental Procedure:

29.27 kg of pure maleic anhydride or 34.65 kg of pure fumaric acid or a mixture of these acids in any proportion or combination, (so that the total quantity of maleic acid or fumaric acid is 34.65 kg—expressed as maleic acid) is taken in 59.5 liters of demineralized water in a separate vessel. To this vessel, aluminum borate is added and stirred well so that the final solution contains 100 mg/l (ppm) of aluminum borate catalyst with respect to the feed taken. The ratio of raw material to catalyst is 1:0001. If necessary, some heating was given to dissolve the catalyst.

This feedstock is charged into the tubular reactor and thoroughly circulated through a hybrid arrangement with another tubular reactor followed by circulation in a stirred tank reactor, all in series, with constant recirculation. The temperature of the solution in the reactor is slowly increased to 145-200° C. and the pressure in the reactor goes up to around 12 bar. Circulation is continued to maintain this condition for quick completion of reaction.

In the case of a batch process, after completion of reaction, the heating is cut off. The reactor in the system is depressurized carefully. Steam is vented out slowly and the pressure also reduces gradually. The temperature of the reactor comes down to about 80-90° C. The whole liquid slurry mass from the reactor vessel is drained completely into a separate vessel. The solution is cooled to ambient temperature. Fumaric acid is separated and the mother liquor containing malic acid, some fumaric acid in solution and a small percentage of unreacted maleic acid is taken for further stages of purification.

In the case of the semi-continuous process, after completion of reaction, 4500 ml of the solution is drained into the flash tank, the reactor pressure reduces to around 10 bar, the same quantity of feed maleic acid solution is fed into the titanium tube assembly, and the reaction is carried out for another 20 minutes and then another 4500 ml solution is drained into the flash tank. This process is continued for several hours and is referred to as a semi-continuous process. After completion, the whole liquid slurry mass from the reactor vessel is drained completely into a separate vessel. The solution is cooled to ambient temperature. After this, the process follows the same steps as a batch process.

In the case of continuous process, after completion of reaction, the solution in the reactor is drained into the flash tank at the rate of 225 ml/min Simultaneously, equal quantity of feed maleic acid solution is fed into the titanium tube. This process is continued for several hours, and the entire liquid slurry mass from the reactor vessel is drained completely into a separate vessel. The solution is cooled to ambient temperature. After this, the process follows the same steps as a batch process.

The above experiments were also carried out without using any catalyst, in all 3 modes of operation—Batch, Semi-continuous, and Continuous. The results of these experiments are shown in Table 2.

Type 2: Without recirculation (Cascade Configuration)
Mode: Batch Process
Batch details:
  Maleic Acid solution: 77 liters (or) Fumaric Acid Solution: 77 liters
  Concentration of Maleic Acid solution/Fumaric acid in water: 45% w/v
  Reaction Temperature: 185° C.
  Reactor Pressure: 12 bar.
  Catalyst: 100 mg/liter (ppm) of Aluminum Borate
Experimental procedure:
The feedstock used in this experiment is defined as any one of the following:
  29.27 kg of pure maleic anhydride dissolved in 60 liters of demineralized water so that the quantity of maleic acid is 34.65 kg.
  34.65 kg of pure fumaric acid.
  A mixture of items 1 and 2 in any proportion or combination in that the quantity of such mixture is equivalent to 34.65 kg of maleic acid.

The setup is made of three stages. The combined reactor volume followed in this experiment is 77 liters. The feedstock is dissolved in 60 liters of demineralized water in feed tank. The above is taken in a separate vessel. To this vessel, aluminum borate catalyst is added and stirred well so that the final solution contains 100 mg/1 (ppm) of aluminum borate catalyst with respect to the feed taken. The ratio of raw material to catalyst is 1:0001. If necessary, some heating was given to dissolve the catalyst.

The feedstock is taken in the first reactor, temperature is raised to 145 to 200° C. and circulated for reaction completion. In the second reactor, the volume of the solution is 17 liters and the reaction is continued. In the third vessel, the reaction duration is higher for completion of reaction. When equilibrium condition between the sequence of operation is reached, the reactors are running continuously without interruption. In all the three reactors, the pressure is around 12 bar and the temperature is 145-200° C. The reaction mixture from the third reactor is drained and the solution is cooled to ambient temperature.

Fumaric acid is separated and the mother liquor containing malic acid, some fumaric acid in solution and a small percentage of unreacted maleic acid is taken for further stages of separation and purification. The exact quantities of malic acid, fumaric acid, and unreacted maleic acid are measured from the quantities obtained and the stoichiometric conversion is calculated.

The above experiment was also carried out without using a catalyst. The results of these experiments are included in Table 2.

Given below Table 2 (2A and 2B) is a table containing the different feedstock compositions, reactor configuration, modes of operation, recirculation, and presence/absence of catalyst and the time taken to achieve equilibrium (reaction duration) for different combinations of these parameters. All reaction conditions such as feedstock concentration, pressure, temperature was for all the sets of experiments and are 45% W/V, 13 bar and 185° C. unless specified otherwise.

TABLE 2A

| | Description Feedstock 1, 2, 3 S. No | | | | | | | |
|---|---|---|---|---|---|---|---|---|
| | 1 | | | 2 | | | 3 | 4 |
| Reactor configuration | Hybrid (Tubular + Tubular + CSTR) | | | Single tubular | | | Cascade (Tubular + Tubular + CSTR in series) Reactor volume = 70 ltr | Single CSTR (reactor volume = 35000 ltr) |
| Catalyst | No | | | No | | | No | No |
| Re-circulation | Yes | | | N/A | | | No | No |
| Mode of operation | B | SC | C | B | SC | C | B | B |
| Reaction duration (in mm.) | 140 | 105 | 70 | 180 | 120 | 90 | 200 | 360 |
| Malic acid produced (kg) | 23.29 | 26.20 | 23.29 | 4.05 | 4.77 | 3.97 | 23.27 | 7562 |
| Malic acid productivity per hour (kg/h) | 9.98 | 14.97 | 19.96 | 1.35 | 2.39 | 2.65 | 6.98 | 1260 |

TABLE 2A-continued

| | Description Feedstock 1, 2, 3 S. No | | | | | | | |
|---|---|---|---|---|---|---|---|---|
| | 1 | | | 2 | | 3 Cascade (Tubular + Tubular + CSTR in series) Reactor volume = 70 ltr | | 4 Single CSTR (reactor volume = 35000 ltr) |
| Reactor con-figuration | Hybrid (Tubular + Tubular + CSTR) | | | Single tubular | | | | |
| Productivity per hour per unit volume of reactor system (kg/h/ltr) | 0.130 | 0.194 | 0.259 | 0.101 | 0.178 | 0.197 | 0.1 | 0.036 |

TABLE 2B

| | Reactor configuration | | | | |
|---|---|---|---|---|---|
| | Hybrid (Tubular + Tubular + CSTR) | | | Cascade (Tubular + Tubular + CSTR in series) | CSTR |
| Mode of operation | B | SC | C | B | B |
| Reaction duration (in min.) With catalyst | 110 | 80 | 55 | 100 | 120 |
| Reaction duration (in min.) Without catalyst | 140 | 105 | 70 | 200 | 360 |

Table 2: Consolidated table showing various feedstock used and the experimental conditions including reaction duration It is clear from Table 2A and 2B that an appreciable increase in productivity per reactor volume was observed with the hybrid and cascade reactor systems in comparison to individual tubular or CSTR reactors respectively. Moreover, reduction in time (i.e., higher reaction kinetics) for the production of malic acid was observed in case of hybrid and cascade reactors in comparison to single tubular and CSTR reactors individually and other conventional methods known in prior-art.

Stoichiometric conversion (Table 3) of feedstock, obtained from all these processes is shown in Table 3. These are nearly the same as that obtained in any batch process, assuming that the total acid quantity before the reaction is 100% maleic acid or 100% fumaric acid or 100% malic acid expressed as maleic acid.

TABLE 3

| | Stoichiometric conversion of feedstock | |
|---|---|---|
| S. No | Name of the Compound | Stoichiometric conversion of Feedstock |
| 1. | Malic Acid | 57 to 58% |
| 2. | Fumaric Acid | 37 to 38% |
| 3. | Maleic Acid | 1.2 to 1.5% |
| 4. | Loss/Unaccounted (CO, $CO_2$ etc.) | 2 to 3% |

Based on experimental data, it may be inferred that the reactor configurations and modes of operation described in serial numbers 1 and 3 in Table 2A improve the productivity of malic and fumaric acids in terms of kg/h of malic acid produced per unit volume (kl) of the reactor system when compared to the conventional methods of operation described in serial numbers 2 and 4 in Table 2A. Table 2B illustrates the effect of catalyst on the overall duration of reaction in both hybrid and cascade reactor systems.

Although the disclosure for production of malic acid is described in language specific to certain embodiments, structures, and methods, it is to be understood that the specific embodiments, structures, and methods are disclosed as examples for implementing the present subject matter.

What is claimed is:

1. A process for production of malic acid, the process comprising:
    (a) obtaining a feed comprising one or more of crude maleic anhydride, pure maleic anhydride, crude maleic acid, crude fumaric acid, pure maleic acid, pure fumaric acid, vent gas scrubber solutions from production of maleic anhydride, and vent gas scrubber solutions from production of phthalic anhydride;
    (b) passing the feed in a tubular reactor assembly to obtain a first product stream comprising unreacted feed and malic acid, wherein the feed is made to undergo hydration reaction in the tubular reactor assembly for a first predetermined time period; and
    (c) causing further hydration of the first product stream in a stirred tank reactor assembly for a second predetermined time period to obtain a final product stream comprising malic acid,
    wherein passing the feed through the tubular reactor assembly comprises passing the feed in a tubular reactor at a Reynolds number from about 2900 to about 10000.

2. The process of claim 1 comprising recirculating a second product stream obtained from the stirred tank reactor assembly through steps (b) and (c) for a predefined number of cycles prior to obtaining the final product stream.

3. The process of claim 1 comprising draining a portion of a second product stream obtained from the stirred tank reactor assembly as the final product stream and recirculating a remaining portion of the second product stream obtained from the stirred tank reactor assembly through steps (b) and (c) along with fresh feed.

4. The process of claim 3, wherein the portion of the second product stream is drained continuously or at predefined time intervals.

5. The process of claim 1, wherein the tubular reactor assembly comprises a single tubular reactor or a plurality of tubular reactors connected in series or parallel or combination of series or parallel connections.

6. The process of claim 1, wherein the stirred tank reactor assembly comprises a single stirred tank reactor or a plurality of stirred tank reactors connected in series or parallel or a combination of series and parallel connections.

7. The process of claim 1 comprising adding a catalyst to the feed prior to passing the feed through the tubular reactor assembly.

8. The process of claim 7, wherein the catalyst is selected from a group consisting of aluminum metal, borate salt of aluminum, and carbonate salt of aluminum.

9. The process of claim 7, wherein the feed to the catalyst weight ratio is in a range of about 1:0.00005 to about 1:0.0005.

10. The process as claimed in claim 5, wherein the feed is reacted at a temperature in a range of about 135-195° C. and a pressure of about 11-15 bar in the single tubular reactor or in each of the plurality of tubular reactor of the tubular reactor assembly.

11. The process as claimed in claim 1 comprising purifying the final product stream to obtain pure malic acid.

12. The process as claimed in claim 1 comprising purifying the feed prior to passing the feed through the tubular reactor assembly.

13. The process as claimed in claim 1 comprising adding steam to the tubular reactor assembly and the stirred tank reactor assembly for causing the hydration reaction.

14. The process as claimed in claim 6, wherein the feed is reacted at a temperature in a range of about 135-195° C. and a pressure of about 11-15 bar in the single stirred tank reactor or in each of the plurality of stirred tank reactor of the stirred tank reactor assembly.

* * * * *